US006262109B1

(12) United States Patent
Clark et al.

(10) Patent No.: US 6,262,109 B1
(45) Date of Patent: Jul. 17, 2001

(54) METHODS OF PREVENTING AND/OR TREATING HIGH SERUM LEVELS OF CHOLESTEROL AND/OR LIPIDS

(75) Inventors: James P. Clark, Naperville; Manfred S. Dunker, Palos Park, both of IL (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 08/849,977

(22) PCT Filed: Dec. 22, 1995

(86) PCT No.: PCT/US95/16774

§ 371 Date: Aug. 22, 1997

§ 102(e) Date: Aug. 22, 1997

(87) PCT Pub. No.: WO96/19217

PCT Pub. Date: Jun. 27, 1996

(51) Int. Cl.$^7$ ................................................. A01N 43/16

(52) U.S. Cl. ..................... 514/458; 514/762; 514/763; 514/824

(58) Field of Search .................... 514/458, 762, 514/763, 824

(56) References Cited

U.S. PATENT DOCUMENTS

| | | | |
|---|---|---|---|
| 3,920,834 | 11/1975 | Kläui et al. | 424/305 |
| 5,208,381 | 5/1993 | Meyer | 568/10 |
| 5,705,526 | * 1/1998 | Fujiwara et al. | 514/458 |
| 5,871,766 | 2/1999 | Hennekens | 424/422 |

FOREIGN PATENT DOCUMENTS

| | | |
|---|---|---|
| 0 600 544 | 6/1994 | (EP) . |
| 0 712 630 | 5/1996 | (EP) . |
| 0 759 294 | 2/1997 | (EP) . |
| 2 698 268 | 5/1994 | (FR) . |
| 2 274 235 | 7/1994 | (GB) . |
| WO 92/05780 | 4/1992 | (WO) . |
| WO 95/00130 | 1/1995 | (WO) . |
| WO 96/19215 | 6/1996 | (WO) . |

OTHER PUBLICATIONS

Tan, D., et al., "Effect of a palm–oil–vitamin–E concentrate on the serum and lipoprotein lipids in humans", The American Journal of Clinical Nutrition, vol. 53, pp. 1027S–30S, (Apr. 1991).
The Merck Index, 11$^{th}$ Ed., p. 884, Entry No. 5492.
Qureshi, A., et al., "Lowering of Serum Cholesterol in Hypercholesterolemic Humans by Tocotrienols (palmvitee)", The American Journal of Clinical Nutrition, vol. 53, pp. 1021S–26S, (Apr. 1991).
Manorama, et al., "Nutritional Evaluation of Crude Palm Oil in Rats", The American Journal of Clinical Nutrition, vol. 53, pp. 1031S–33S, (Apr. 1991).
Tan, B., et al., "Hydrocarbon Carotenoid Profiles of Palm Oil Processed Fractions", JAOCS, vol. 63(9), pp. 1175–1179, (Sep. 1986).
Tan, B., et al., "Palm Carotenoids, Tocopherols and Tocotrienols", JAOCS, vol. 66(6), pp. 770–776, (Jun. 1989).
Sundram, K., et al., "Replacement of Dietary Fat with Palm Oil: Effect on Human Serum Lipids, Lipoproteins and Apolipoproteins.", Brit. J. Nutr., vol. 68, pp. 677–692, (1992).
Hermann, W., et al., "The Effect of Tocopherol on High-–Density Lipoprotein Cholesterol.", Am. Soc. Cl. Pathol., vol. 72, pp. 848–852, (1979).
P. Fahey, M.D., et al., "Disease Prevention Through Adulthood and Old Age", Key Issues in Nutrition, vol. 82(1), pp. 135–142, (Jul. 1987).
DiMascio, P., et al., "Carotenoids, Tocopherols and Thiols as Biological Singlet Molecular Oxygen Quenchers", Biochem. Soc. Trans., vol. 18, pp. 1054–1056, (1990).
Y.M. Choo, et al.: "Production of Palm Oil Carotenoid Concentrate And Its Potential Application In Nutrition", Lipid–Soluble Antioxidants, 1992, pp. 243–254, XP–002120457.
A. Carughi, et al.,: "Plasma Carotenoid Concentrations Before and After Supplementation With A Carotenoid Mixture", American Journal of Clinical Nutrition, vol. 59, No. 4, Apr., 1994, pp. 896–899, XP002120458.
J.W. Erdman, et al.: "Failure Of The Non–Vitamin A Active Carotenoid Lycopene To Act As An Antihypercholesterolemic Agent In Rats", Nutrition Reports International, vol. 10, No. 5, 1974, pp. 277–284, XP002116940.
Stampfer et al., "Vitamin E Consumption and The Risk of Coronary Disease in Women", *The New England Journal of Medicine*, 328: 1444–9 (1993).
Rimm et al., "Vitamin E Consumption and The Risk of Coronary Disease in Men", *The New England Journal of Medicine*, 328: 1450–6 (1993).
Kardinaal et al., "Antioxidants in Adipose Tissue and Risk of Myocardial Infarction: The Euramic Study," *Lancet*, 342:1379–84 (1993).

(List continued on next page.)

Primary Examiner—Theodore J. Criares
(74) Attorney, Agent, or Firm—John E. Drach; Glenn J. Murphy; Aaron R. Ettelman

(57) ABSTRACT

A method for preventing or treating high serum levels of cholesterol and lipids in a mammal, said method comprising orally administering an effective amount of natural lycopene to prevent or treat high serum levels of cholesterol or lipids to a mammal in need of such treatment. Also disclosed is an oral pharmaceutical composition in unit dosage form for oral administration for the prevention or treatment of high serum levels of cholesterol and/or lipids in a mammal, said composition comprising an effective amount of natural lycopene to prevent or treat high serum levels of cholesterol or lipids in a mammal and in a sufficient amount to achieve a level of serum cholesterol of less than 200 mg per deciliter over the course of treatment, and a pharmaceutically acceptable carrier therefor.

7 Claims, No Drawings

OTHER PUBLICATIONS

Gaziano et al., "Beta Carotene Therapy for Chronic Stable Angina", *Circulation*, 82:III, Abstract No. 0796 (1990).
JAMA, 251:351–64, 1984.
Levy et al., *Circulation*,69:325–37 (1984).

Blankenhorn et al., JAMA, 257:3233–40, 1987.

Remington's Pharmaceutical Sciences—Chapters 89–91, pp. 1632–1692 (1990).

* cited by examiner

METHODS OF PREVENTING AND/OR TREATING HIGH SERUM LEVELS OF CHOLESTEROL AND/OR LIPIDS

CROSS-REFERENCE TO RELATED APPLICATIONS

This application is a 35 U.S.C. §371 national stage application based upon International Application No. US95/16774, filed on Dec. 22, 1995, which in turn claimed priority, under 35 U.S.C. §120, as a continuation-in-part of U.S. patent application no. 08/362,617, filed on Dec. 22, 1994 (now abandoned).

FIELD OF THE INVENTION

The present invention relates to the prevention or treatment of cardiovascular disease and more particularly to natural compositions which exert a protective action on the cardiovascular system against high levels of serum lipid and/or cholesterol. More particularly, the present invention relates to pharmaceutical compositions comprising a protective amount of natural lycopene, i.e., an amount of lycopene which protects the body against risks of high levels of cholesterol and/or lipid. The present invention is also directed to methods that prevent high serum lipid and cholesterol levels in a mammal, including humans, thereby lowering the risks of developing cardiovascular disease.

BACKGROUND OF THE INVENTION

Reduction of cholesterol greatly lowers the incidence of cardiovascular disease. Thus, it has been reported in *JAMA* 1984; 251:351–64 that lowering of serum cholesterol levels with drugs prevents heart attacks. Coronary angiographic studies have also demonstrated the benefits of lower serum cholesterol in the prevention of coronary heart disease. See, for example, Levy et al, *Circulation,* 69:32S–37 (1984). Other studies also reported the benefits of lower cholesterol in slowing the growth of atherosclerotic lesions. See, for example, Blankenhom et al., *JAMA,* 257:323340 (1987).

The drugs which are being used in these studies are, for example, clofibrate, gemfibrozil, fenofibrate and bezafibrate or a combination of cholestyramine and niacin. These reports clearly support the theory that lowering of serum cholesterol level will retard coronary atherogenesis and therefore reduce the risk of cardiovascular disease.

One of the problems with the therapy described above is that they are all pharmaceutical compounds which tend to require a long course of therapy. Unfortunately, considerable undesirable side effects are experienced by a number of patients.

Several therapeutic approaches for using vitamin E have been proposed. One such approach is described in the articles, "Vitamin E Consumption And The Risk Of Coronary Disease In Women" by Stampfer et al., *The New England Journal of Medicine,* 328: 1444–9 (1993), and "Vitamin E Consumption And The Risk of Coronary Heart Disease In Men" by Rimm et al., *The New England Journal of Medicine,* 328: 1450–6 (1993), which disclose that oxidation of low-density lipoprotein (LDL) plays a role in atherosclerosis. It appears that the oxidation of LDL increases their incorporation into the arterial intima which is an essential step in atherogenesis.

Thus, in the foregoing articles, investigators have studied the effect of taking vitamin E and the risk of coronary disease and observed that the use of vitamin E supplements in middle-aged women is associated with a reduced risk of coronary heart disease. Similarly, an association between a high intake of vitamin E and a lower risk of coronary heart disease was also observed in men.

In another study reported in *Lancet,* 342: 1379–84 (1993), it was observed that high beta-carotene intake reduced the risk of myocardial infarction. Beta-carotene has also been suggested as useful in reducing vascular events in patients with chronic stable angina. See, Gaziano et al., "Beta Carotene Therapy for Chronic Stable Angina," *Circulation* 82:III, Abstract No. 0796 (1990).

In spite of the foregoing attempts to develop a method for preventing or treating high levels of serum cholesterol and/or lipids, there still exists a need in the art for a composition and method for protecting a mammal, including humans, against high serum cholesterol and lipid levels without the disadvantages and side effects associated with conventional drug therapy.

SUMMARY OF THE INVENTION

Surprisingly, the present inventors have now found that a patient can be protected against the development of cardiovascular disease without the use of conventional drug therapy by the compositions and methods of the present invention. The compositions of the present invention comprise as an active ingredient an effective protective amount of natural lycopene in an inert pharmaceutically acceptable carrier. The composition comprises an amount of natural lycopene which protects the body against the risks of high levels of serum cholesterol and lipid.

Generally, the method comprises the step of administering to a mammal, including humans, in need of preventing or treating high levels of serum cholesterol or lipids, the composition of the present invention. The composition is preferably administered until the serum cholesterol is reduced and maintained at less than 200 mg per decaliter.

DETAILED DESCRIPTION OF THE PREFERRED EMBODIMENTS OF THE INVENTION

According to the present invention, the inventors have discovered a composition in unit dosage form which protects the body against high serum cholesterol and lipid levels. These compositions comprise as an active ingredient an effective amount of natural lycopene to prevent or treat high levels of serum cholesterol and lipids.

Lycopene is a natural red carotinoid which occurs for example in tomatoes. It can also be produced synthetically. See for example U.S. Pat. No. 5,208,381. However, it is natural lycopene which is intended in the practice of the present invention.

Generally speaking to have the desired protective action a dose of approximately 1 mg to approximately 10 mg daily for a 70 kg adult is suggested until the cholesterol level is lowered to less than 200 mg per deciliter. The precise amount of natural lycopene administered to a patient, of course, depends on a wide variety of factors such as the age and overall health of the patient, whether other pharmaceuticals and nutritionals being administered, and the like. It will be realized that if the patient has been diagnosed for advanced stages of atherosclerosis, that is, treatment of an ongoing condition, dosages at the higher end of this range is suggested. However, if only for the protective or preventive action, dosage at the lower end may be sufficient.

To broaden and enhance the therapeutic spectrum of the compositions of the present invention, other known naturally occurring substances may be included. These include, for example, natural beta-carotene. Alternatively, lycopene can be combined with natural tocopherol, especially alpha-tocopherol, with or without natural beta-carotene. The natural beta-carotene is preferably obtained from natural sources, such as palm oil or algae.

Beta-carotene, provitamin A, is readily metabolized by the body into vitamin A when required. There is also increasing evidence which suggests that there is a therapeutic benefit to beta-carotene itself, independent of vitamin A activity.

The primary source of the beta-carotene is an algae named *Dunaliella salina*. The algal cell functions just like an ordinary plant cell. It is photosynthetic, converting carbon dioxide from the atmosphere into cell material and to provide energy. This is done by the green chlorophyll in the cell which is normally not visible as it is masked by the intense orange color of the beta-carotene.

Natural beta-carotene from the algae comprises an approximately equal mixture of cis and trans isomers with the cis form of beta carotene being more soluble in oil than synthetic trans beta carotene.

Synthetic beta-carotene is derived from synthetic organic chemicals and is a crystalline form of beta-carotene, primarily the trans isomer (a molecular configuration). The synthetic form is not the focus of the present invention which is directed to natural source products because of the advantages associated with their use.

The synthetic crystals of beta-carotene are difficult to dissolve in organic chemical solvents, implying that the human body would have similar, or greater, difficulties in assimilating the compound.

The natural carotenoids are mixture of compounds. Those include beta-carotene, alpha-carotene, lutein, cryptoxanthin, zeaxanthin and lycopene.

The natural carotinoids are a mixture of cis and trans isomers while the synthetic carotenoids are all trans isomers.

Betatene, natural mixed carotenoids, is a registered trademark of Betatene Ltd. and is particularly useful in the practice of the present invention.

Betatene is a deep red suspension of natural mixed carotenoids in vegetable oil. The mixed carotenoids are isolated from the sea algae *Dunaliella salina*.

Betatene, natural beta-carotene, is soluble in oil to about 3.7% or about ten times the solubility of synthetic oil suspensions. This indicates a higher degree of bioavailability in the body.

The carotenoid content of Betatene 20% is standardized to contain not less than 200 mg per gram of five naturally occurring carotenoids that are commonly found in various fruits, cruciferous, yellow, and dark green leafy vegetables. The typical carotenoid distribution in Betatene 20% is as follows:

|  | 200 mg/gram |
| --- | --- |
| beta-carotene | 190,500 mcg |
| alpha-carotene | 6,000 mcg |
| zeaxanthin | 1,200 mcg |
| cryptoxanthin | 1,400 mcg |
| lutein | 900 mcg |

In addition to its role as an antioxidant, the beta-carotene provided by Betatene 20%, is a safe source of vitamin A, being converted to vitamin A within the body only as needed.

The amount of carotene or beta-carotene useful in the practice of the present invention can vary over a wide range and can be readily determined by one skilled in the art. Generally, the amount of carotene or beta-carotene is an amount sufficient to complement the lycopene and is an effective amount to prevent or treat high levels of serum cholesterol and/or lipids.

A similar amount of natural tocopherol is useful in the practice of the present invention. Natural tocotrienols and natural tocopherols are derived from vegetable oils. Soy oil is the most widely used source. Sunflower, corn, peanut, rapeseed and cottonseed oils may also be used. Natural tocotrienol and natural tocopherols are very different from that produced by chemical synthesis, i.e., synthetic "vitamin E." While the definition of vitamin E is not consistent, for the purposes of the present invention, vitamin E refers to both tocotrienols and tocopherols.

Synthetic vitamin E is a mixture of eight different stereoisomers, only one of which is molecularly equivalent to natural vitamin E. The other seven stereoisomers have a lower biological activity. The mammalian body prefers the natural stereoisomer.

Natural vitamin E is recognized as having 36 percent greater potency than synthetic vitamin E. Recent studies suggest that natural vitamin E is probably twice as effective as synthetic vitamin E.

Natural vitamin E also remains in the body much longer than synthetic vitamin E. The seven synthetic stereoisomers are secreted into the bile and then into the intestine for removal from the body. The natural vitamin E stereoisomer, on the other hand, is returned to the bloodstream in the form of low density lipoproteins.

Any natural tocopherol or tocotrienol, its ester or compounds convertible to either tocopherols or their esters are suitable for use in the practice of the present invention.

The prior art has failed to appreciate any benefit associated with the administration of lycopene and/or tocotrienols or tocopherols to a mammal, including humans, to prevent the harmful effects of high serum cholesterol and lipid levels. Further, the prior art has heretofore never recognized any benefit for such a method using natural lycopene and/or natural tocotrienols or natural tocopherols.

The oral compositions of the present invention can be made by conventional compounding procedures known in the pharmaceutical art, that is, by mixing the active substances with edible pharmaceutically acceptable non-toxic inert, solid or liquid carriers and/or excipients suitable for systemic administration and conventionally used in oral dosage forms. Additionally, edible, non-toxic pharmaceutically acceptable stabilizers usually used as stabilizers in oral dosage forms or edible, non-toxic pharmaceutically acceptable salts thereof can be included in the compositions of the present invention. All the above carriers, excipients and stabilizers are intended to include only those suitable for oral administration and all are conventional and known to the pharmaceutical compounding art.

The compositions for oral administration comprise a pharmaceutically acceptable and otherwise inert carrier. Thus, for example, when administered orally, the active ingredient is formulated in the form of soft gelatin capsule, elixir, emulsion and the like employing methods well known in the art. Suitable formulations and formulation techniques can be found in *Remington's Pharmaceutical Sciences*, eighteenth edition, 1990, by Mack Publishing Company.

The preferred method for administering the compositions of this invention is the oral route of administration. Typically lycopene is formulated in the form of a capsule as described more fully in the following example. The patient ingests this capsule, preferably on a daily basis.

In order to illustrate the practice of the present invention, the following non-limiting example is provided. It will be appreciated that a vast number of additional compositions fall within the scope of the present invention. The Example is provided by way of illustration only and is not intended to limit the invention in any way.

EXAMPLE 1

About 5 mg units of lycopene is mixed in a suitable blender with about 450 mg of peanut oil. It is then dispensed in the form of soft gelatin capsule.

EXAMPLE 2

The same mixture is used as in Example 1 except there is added 5 mg of beta-carotene.

EXAMPLE 3

The same mixture is used as in Example 1 except there is added about 5 mg beta-carotene and 400 IU of alpha-tocopherol.

What is claimed is:

1. A method for preventing or treating high serum levels of cholesterol and/or lipids in a mammal, said method comprising orally administering an effective amount of natural lycopene to prevent or treat high serum levels of cholesterol or lipid to a mammal in need of such prevention or treatment.

2. The method according to claim 1 wherein approximately 1 mg to approximately 10 mg of natural lycopene is administered.

3. The method according to claim 1 further comprising administering a natural carotenoid.

4. The method according to claim 3 wherein said natural carotenoid is natural beta-carotene.

5. The method according to claim 1 further comprising administering natural tocopherol.

6. The method according to claim 5 wherein the natural tocopherol is natural alpha-tocopherol.

7. A method for treating hypercholesterolemia in a patient in need thereof, which comprises:

administering to said patient a hypercholesterolemia therapeutic agent containing natural lycopene as an effective ingredient therein, wherein said lycopene is administered to said patient in an amount within a range of from 1 to 25 mg per day per adult.

* * * * *